United States Patent
He et al.

(10) Patent No.: US 6,957,012 B2
(45) Date of Patent: Oct. 18, 2005

(54) METHOD AND APPARATUS FOR DUAL-OUTLET VAPOR DISPENSER

(75) Inventors: Mengtao Pete He, Scottsdale, AZ (US); Carl Triplett, Scottsdale, AZ (US); Mary Conway, Phoenix, AZ (US)

(73) Assignee: The Dial Corporation, Scottsdale, AZ (US)

(*) Notice: Subject to any disclaimer, the term of this patent is extended or adjusted under 35 U.S.C. 154(b) by 0 days.

(21) Appl. No.: 10/993,848

(22) Filed: Nov. 19, 2004

(65) Prior Publication Data

US 2005/0069306 A1 Mar. 31, 2005

Related U.S. Application Data

(63) Continuation of application No. 10/640,140, filed on Aug. 13, 2003, now Pat. No. 6,832,794, and a continuation-in-part of application No. 10/222,501, filed on Aug. 16, 2002.

(51) Int. Cl.⁷ .................................................. F24F 6/00
(52) U.S. Cl. ...................................... 392/392; 392/395
(58) Field of Search .................... 392/392, 394, 392/395; 239/34, 44, 45, 135, 136; 261/141, 142, DIG. 65; 337/186, 197, 198, 255, 259, 269

(56) References Cited

U.S. PATENT DOCUMENTS

| | | |
|---|---|---|
| 1,836,600 A | 12/1931 | Jones |
| 2,636,096 A | 4/1953 | Di Blasi |
| 2,792,561 A | 5/1957 | Cohen |
| 3,262,290 A | 7/1966 | Huber |
| 3,748,438 A | 7/1973 | Costello |
| 3,780,260 A | 12/1973 | Eisner |
| 3,895,928 A | 7/1975 | Gonzalo |
| 3,908,905 A | 9/1975 | Von Philipp et al. |
| 3,923,458 A | 12/1975 | Gonzalo |

(Continued)

FOREIGN PATENT DOCUMENTS

| | | |
|---|---|---|
| DE | 35 35 564 | 5/1986 |
| DE | 41 31 613 | 3/1993 |
| DE | 0 669 137 | 8/1995 |
| EP | 0 296 807 | 12/1988 |
| EP | 0 911 041 | 4/1999 |
| GB | 402507 | 12/1933 |
| GB | 2 356 815 | 6/2001 |
| WO | WO 00 76292 | 12/2000 |
| WO | WO 01 10739 | 2/2001 |
| WO | WO 01/68154 | 9/2001 |
| WO | WO 01/93919 | 12/2001 |

OTHER PUBLICATIONS

PCT International Search Report issued Dec. 17, 2003 for International Application No. PCT/US03/26511, International Filing Date Aug. 26, 2003, 4 pages.

PCT Written Opinion issued Nov. 22, 2004 for International Application No. PCT/US03/26511, International Filing Date Aug. 26, 2003, 6 pages.

PCT International Search Report issued Apr. 21, 2004 for International Application No. PCT/US03/26754, International Filing Date Aug. 28, 2003, 6 pages.

(Continued)

*Primary Examiner*—Sang Y. Paik
(74) *Attorney, Agent, or Firm*—Snell & Wilmer LLP

(57) ABSTRACT

A multiple-outlet vapor-dispensing device is configured to interface with an electrical receptacle such that the functionality of that outlet is substantially maintained. In accordance with one aspect of the present invention, a vapor-dispensing device is configured to connect to an electrical receptacle having at least one outlet. The vapor-dispensing device comprises a housing having a first device outlet and a second device outlet, the housing being attachable to the outlet.

3 Claims, 7 Drawing Sheets

U.S. PATENT DOCUMENTS

| | | |
|---|---|---|
| 3,948,445 A | 4/1976 | Andeweg |
| 4,017,030 A | 4/1977 | Coplan et al. |
| 4,037,353 A | 7/1977 | Hennart et al. |
| 4,084,079 A | 4/1978 | Costello |
| 4,111,655 A | 9/1978 | Quincey |
| 4,123,741 A | 10/1978 | Kiyono et al. |
| 4,165,835 A | 8/1979 | Dearling |
| 4,171,340 A | 10/1979 | Nishimura et al. |
| 4,208,012 A | 6/1980 | Dutcher |
| 4,214,146 A | 7/1980 | Schimanski |
| 4,220,281 A | 9/1980 | Martens, III et al. |
| 4,228,124 A | 10/1980 | Kashihara et al. |
| 4,243,969 A | 1/1981 | Steigerwald et al. |
| 4,293,173 A | 10/1981 | Tricca |
| 4,294,778 A | 10/1981 | DeLuca |
| 4,346,059 A | 8/1982 | Spector |
| 4,391,781 A | 7/1983 | van Lit |
| 4,408,813 A | 10/1983 | Koehler |
| 4,413,779 A | 11/1983 | Santini |
| 4,415,797 A | 11/1983 | Choustoulakis |
| 4,425,302 A | 1/1984 | Pons Pons |
| 4,467,117 A | 8/1984 | Lund et al. |
| 4,518,212 A | 5/1985 | Rumble |
| 4,530,556 A | 7/1985 | Bonus |
| 4,537,351 A | 8/1985 | Wilson |
| 4,544,592 A | 10/1985 | Spector |
| 4,549,250 A | 10/1985 | Spector |
| 4,556,539 A | 12/1985 | Spector |
| 4,571,485 A | 2/1986 | Spector |
| 4,574,181 A | 3/1986 | Spector |
| 4,595,564 A | 6/1986 | Spector et al. |
| 4,631,387 A | 12/1986 | Glucksman |
| 4,658,985 A | 4/1987 | Madsen et al. |
| 4,660,764 A | 4/1987 | Joyaux et al. |
| 4,662,679 A | 5/1987 | Franck et al. |
| 4,675,504 A | 6/1987 | Suhajda |
| 4,686,353 A | 8/1987 | Spector |
| 4,695,434 A | 9/1987 | Spector |
| 4,703,155 A | 10/1987 | Suhajda |
| 4,707,336 A | 11/1987 | Jones |
| 4,714,984 A | 12/1987 | Spector |
| 4,718,856 A | 1/1988 | Pinkerton et al. |
| 4,725,712 A | 2/1988 | Schroeder |
| 4,731,520 A | 3/1988 | Glucksman et al. |
| 4,731,522 A | 3/1988 | Manchester |
| 4,732,321 A | 3/1988 | Dolan |
| 4,734,560 A | 3/1988 | Bowen |
| 4,739,928 A | 4/1988 | O'Neil |
| 4,743,406 A | 5/1988 | Steiner et al. |
| 4,753,389 A | 6/1988 | Davis |
| 4,777,345 A | 10/1988 | Manchester |
| 4,780,286 A | 10/1988 | Parent et al. |
| 4,795,883 A | 1/1989 | Glucksman et al. |
| 4,798,935 A | 1/1989 | Pezaris |
| 4,800,239 A | 1/1989 | Hill |
| 4,801,271 A | 1/1989 | Piper |
| 4,804,821 A | 2/1989 | Glucksman |
| 4,808,347 A | 2/1989 | Dawn |
| 4,816,973 A | 3/1989 | Atalla et al. |
| 4,830,791 A | 5/1989 | Muderlak et al. |
| 4,837,421 A | 6/1989 | Luthy |
| 4,849,606 A | 7/1989 | Martens, III et al. |
| 4,853,517 A | 8/1989 | Bowen et al. |
| 4,878,615 A | 11/1989 | Losi |
| 4,886,469 A | 12/1989 | Jseng |
| 4,915,301 A | 4/1990 | Munteanu |
| 4,919,981 A | 4/1990 | Levey et al. |
| 4,931,224 A | 6/1990 | Holzner, Sr. |
| 4,931,258 A | 6/1990 | Zlotnik et al. |
| 4,968,456 A | 11/1990 | Muderlak et al. |
| D315,789 S | 3/1991 | Muderlak |
| 4,998,671 A | 3/1991 | Leifheit |
| 5,004,435 A | 4/1991 | Jammet |
| 5,014,913 A | 5/1991 | Hoyt et al. |
| 5,015,442 A | 5/1991 | Hirai |
| 5,029,729 A | 7/1991 | Madsen et al. |
| 5,038,394 A | 8/1991 | Hasegawa et al. |
| 5,050,798 A | 9/1991 | Sullivan |
| 5,106,317 A | 4/1992 | Taylor |
| 5,111,477 A | 5/1992 | Muderlak |
| 5,115,975 A | 5/1992 | Shilling |
| 5,121,881 A | 6/1992 | Lembeck |
| 5,126,078 A | 6/1992 | Steiner et al. |
| 5,136,684 A | 8/1992 | Lonker et al. |
| 5,147,582 A | 9/1992 | Holzner, Sr. et al. |
| 5,148,984 A | 9/1992 | Bryson, Jr. et al. |
| 5,175,791 A | 12/1992 | Muderlak et al. |
| 5,196,171 A | 3/1993 | Peltier |
| 5,201,025 A | 4/1993 | Landesberg |
| 5,217,696 A | 6/1993 | Wolverton et al. |
| 5,220,636 A | 6/1993 | Chang |
| 5,222,186 A | 6/1993 | Schimanski et al. |
| 5,223,182 A | 6/1993 | Steiner et al. |
| 5,233,680 A | 8/1993 | Fussell |
| 5,239,610 A | 8/1993 | Shao |
| 5,240,426 A | 8/1993 | Barla |
| 5,285,014 A | 2/1994 | Gilchrist |
| 5,290,546 A | 3/1994 | Hasegawa et al. |
| 5,295,845 A | 3/1994 | Changxing |
| 5,314,669 A | 5/1994 | Hamilton |
| 5,320,542 A | 6/1994 | Cheng |
| 5,339,065 A | 8/1994 | Slenker |
| 5,342,584 A | 8/1994 | Fritz et al. |
| 5,373,581 A | 12/1994 | Smith |
| 5,375,728 A | 12/1994 | West |
| 5,376,338 A | 12/1994 | Zlotnik |
| 5,382,410 A | 1/1995 | Peltier |
| D355,251 S | 2/1995 | Paulovich et al. |
| 5,394,506 A | 2/1995 | Stein et al. |
| 5,402,517 A | 3/1995 | Gillett et al. |
| D357,330 S | 4/1995 | Wong et al. |
| 5,431,859 A | 7/1995 | Tobin |
| 5,431,885 A | 7/1995 | Zlotnik et al. |
| 5,445,802 A | 8/1995 | Wendelken |
| 5,465,198 A | 11/1995 | Kellogg |
| 5,480,591 A | 1/1996 | Lagneaux et al. |
| 5,481,442 A | 1/1996 | Wiltshire et al.. |
| 5,484,086 A | 1/1996 | Pu |
| 5,498,397 A | 3/1996 | Horng |
| 5,521,357 A | 5/1996 | Lock et al. |
| 5,522,008 A | 5/1996 | Bernard |
| 5,547,616 A | 8/1996 | Dancs et al. |
| 5,556,192 A | 9/1996 | Wang |
| 5,567,361 A | 10/1996 | Harper |
| 5,574,821 A | 11/1996 | Babasade |
| 5,575,992 A | 11/1996 | Kunze |
| 5,577,156 A | 11/1996 | Costello |
| 5,591,395 A | 1/1997 | Schroeder et al. |
| 5,624,230 A | 4/1997 | Taylor et al. |
| 5,634,806 A | 6/1997 | Hahn |
| 5,647,052 A | 7/1997 | Patel et al. |
| 5,647,053 A | 7/1997 | Schroeder et al. |
| 5,651,942 A | 7/1997 | Christensen |
| 5,662,835 A | 9/1997 | Collingwood |
| 5,664,958 A | 9/1997 | Chadwick et al. |
| 5,700,430 A | 12/1997 | Bonnema et al. |
| 5,735,460 A | 4/1998 | Eisenbraun |
| 5,749,520 A | 5/1998 | Martin et al. |
| 5,750,498 A | 5/1998 | Soeda et al. |
| 5,765,751 A | 6/1998 | Joshi |
| 5,788,155 A | 8/1998 | Martin et al. |

| | | |
|---|---|---|
| 5,788,931 A | 8/1998 | Munoz Quintana |
| 5,796,914 A | 8/1998 | Gatzemeyer et al. |
| 5,805,768 A | 9/1998 | Schwartz et al. |
| 5,810,265 A | 9/1998 | Cornelius et al. |
| 5,813,873 A | 9/1998 | McBain et al. |
| 5,816,492 A | 10/1998 | Charles et al. |
| 5,832,648 A | 11/1998 | Malone |
| 5,873,529 A | 2/1999 | Johnson |
| 5,875,968 A | 3/1999 | Miller et al. |
| 5,884,808 A | 3/1999 | Muderlak et al. |
| 5,899,381 A | 5/1999 | Gordon et al. |
| 5,903,710 A | 5/1999 | Wefler et al. |
| 5,926,614 A | 7/1999 | Steinel |
| 5,928,605 A | 7/1999 | Bonnema et al. |
| 5,932,204 A | 8/1999 | Joshi |
| 5,937,140 A | 8/1999 | Leonard et al. |
| 5,940,577 A | 8/1999 | Steinel |
| 5,944,223 A | 8/1999 | Klima et al. |
| 5,945,094 A | 8/1999 | Martin et al. |
| 5,955,701 A | 9/1999 | Schockner et al. |
| 5,957,701 A | 9/1999 | McMillin |
| 5,970,643 A | 10/1999 | Gawel, Jr. |
| 5,976,503 A | 11/1999 | Martin et al. |
| 5,998,735 A | 12/1999 | Patterson, Jr. |
| 6,021,254 A | 2/2000 | Hunter |
| 6,031,967 A | 2/2000 | Flashinski et al. |
| 6,032,930 A | 3/2000 | Calino |
| 6,036,536 A | 3/2000 | Chiu |
| 6,044,202 A | 3/2000 | Junkel |
| 6,045,374 A | 4/2000 | Candeloro |
| 6,050,551 A | 4/2000 | Anderson |
| 6,051,788 A | 4/2000 | Nichols |
| 6,078,728 A | 6/2000 | O'Rourke et al. |
| 6,085,026 A | 7/2000 | Hammons et al. |
| 6,097,881 A | 8/2000 | DeWitt et al. |
| 6,099,137 A | 8/2000 | McCormick et al. |
| 6,101,315 A | 8/2000 | Steinel, Jr. |
| 6,104,866 A | 8/2000 | DeWitt et al. |
| 6,104,867 A | 8/2000 | Stathakis et al. |
| D430,659 S | 9/2000 | Zaragoza et al. |
| 6,123,935 A | 9/2000 | Wefler et al. |
| 6,141,496 A | 10/2000 | Sundberg et al. |
| 6,148,143 A | 11/2000 | Steinel, Jr. |
| 6,156,088 A | 12/2000 | Cardarelli |
| 6,197,262 B1 | 3/2001 | Del Ben |
| 6,197,263 B1 | 3/2001 | Blount |
| 6,227,118 B1 | 5/2001 | Nance |
| 6,236,807 B1 | 5/2001 | Ruffolo et al. |
| 6,249,645 B1 | 6/2001 | Smith |
| 6,254,065 B1 | 7/2001 | Ehrensperger et al. |
| 6,264,548 B1 | 7/2001 | Payne, Jr. et al. |
| 6,269,979 B1 | 8/2001 | Dumont |
| 6,270,720 B1 | 8/2001 | Mandish |
| 6,275,651 B1 | 8/2001 | Voit |
| 6,278,840 B1 | 8/2001 | Basaganas Millan |
| 6,285,830 B1 | 9/2001 | Basaganas Millan |
| 6,289,176 B1 | 9/2001 | Martter et al. |
| 6,302,559 B1 | 10/2001 | Warren |
| 6,315,959 B2 | 11/2001 | Mandish |
| 6,328,791 B1 | 12/2001 | Pillion et al. |
| 6,342,676 B1 | 1/2002 | Ha |
| 6,349,168 B1 | 2/2002 | Jaworski |
| 6,352,210 B1 | 3/2002 | Requejo |
| 6,354,513 B1 | 3/2002 | Basaganas Millan |
| 6,361,752 B1 | 3/2002 | Demarest et al. |
| 6,364,673 B1 | 4/2002 | Lee |
| 6,368,564 B1 | 4/2002 | Smith |
| 6,371,815 B1 | 4/2002 | Wetzel et al. |
| 6,374,044 B1 | 4/2002 | Freidel |
| 6,374,045 B2 | 4/2002 | Basaganas Millan |
| 6,381,408 B1 | 4/2002 | Jaworski et al. |
| 6,603,924 B2 | 8/2003 | Brown et al. |
| 6,714,725 B2 | 3/2004 | Grone et al. |
| 6,832,794 B2 * | 12/2004 | He et al. .................... 392/392 |
| 6,853,801 B2 * | 2/2005 | Wefler ....................... 392/392 |
| 2001/0031225 A1 | 10/2001 | Mandish |
| 2001/0053283 A1 | 12/2001 | Levine et al. |
| 2002/0144992 A1 | 10/2002 | Viera |
| 2003/0138241 A1 | 7/2003 | Ambrosi et al. |

OTHER PUBLICATIONS

PCT International Preliminary Examination Report issued Jul. 20, 2004 for International Application No. PCT/US03/26754, International Filing Date Aug. 28, 2003, 3 pages.

PCT International Search Report issued Nov. 12, 2003 for International Application No. PCT/US03/25245, International Filing Date Aug. 13, 2003, 4 pages.

PCT Written Opinion issued Jul. 19, 2004 for International Application No. PCT/US03/25245, International Filing Date Aug. 13, 2003, 5 pages.

PCT International Preliminary Examination Report issued Nov. 29, 2004 for International Application No. PCT/US03/25245, International Filing Date Aug. 13, 2003, 4 pages.

PCT International Search Report issued Oct. 7, 2003 for International Application No. PCT/US03/04082, International Filing Date Feb. 12, 2003, 8 pages.

PCT Written Opinion issued Mar. 5, 2004 for International Application No. PCT/US03/04082, International Filing Date Feb. 12, 2003, 4 pages.

PCT International Preliminary Examination Report issued May 25, 2004 for International Application No. PCT/US03/04082, International Filing Date Feb. 12, 2003, 13 pages.

PCT International Search Report issued Dec. 16, 2003 for International Application No. PCT/US03/25244, International Filing Date Aug. 13, 2003, 3 pages.

PCT Written Opinion issued Jul. 15, 2004 for International Application No. PCT/US03/25244, International Application No. PCT/US03/25246, International Filing Date Aug. 13, 2003, 4 pages.

PCT International Search Report issued Dec. 19, 2003 for International Application No. PCT/US03/25243, International Filing Date Aug. 13, 2003, 4 pages.

PCT Written Opinion issued Sep. 17, 2004 for International Application No.PCT/US03/25243, International Filing Date Aug. 13, 2003, 4 pages.

Brochure– "Decora Devices," by Leviton, date unknown, Section A, pps. A1–A36.

PCT International Preliminary Examination Report issued Jan. 21, 2005 for International Application No. PCT/US03/25246, International Filing Date Aug. 13, 2003, 6 pages (citations previously disclosed in prior IDS).

* cited by examiner

METHOD AND APPARATUS FOR DUAL-OUTLET VAPOR DISPENSER

CROSS-REFERENCE TO RELATED APPLICATIONS

This application is a continuation of U.S. patent application Ser. No. 10/222,501 entitled "Methods and Apparatus for Dual-Outlet Vapor Dispenser" filed Aug. 16, 2002 and U.S. patent application Ser. No. 10/640,140 entitled Method and Apparatus for a Dual-Outlet Vapor-Dispenser filed Aug. 13, 2003 now U.S. Pat. No. 6,832,794 which are incorporated herein by reference.

FIELD OF INVENTION

The present invention generally relates to vapor-dispensing devices and, more particularly, to a multiple-outlet vapor-dispensing device.

BACKGROUND OF THE INVENTION

Vapor-dispensing products typically include a volatizable material and a transport system configured to facilitate evaporation of the volatizable material into the surrounding air. For example, in some systems, a liquid is contained in a reservoir bottle; in others, a wax material is used. The housing, which protrudes from a wall outlet, facilitates the evaporation of the volatizable material into the environment. In such devices, a heating element may deliver kinetic energy to molecules of the liquid as contained in the wick. Such units are plugged into a conventional electrical outlet, thereby causing the heating element to heat the liquid and vaporize liquid that has been drawn up into the wick.

Known vapor-dispensing devices of this type may be unsatisfactory in a number of respects. For example, various vapor-dispensing devices (e.g., room freshener's and the like) that interface with wall outlets may lack stability, may be undesirably noticeable, and/or may obstruct access to and use of one or more of the wall outlets. That is, one disadvantage of known vapor dispensers is that, when it is plugged into a wall outlet, the ability to use the electrical outlet or outlets into which it is plugged is reduced or eliminated by the virtue of dispenser geometry or other factors.

Thus, there is a need for a vapor-dispensing device that overcomes these and other limitations of the prior art.

SUMMARY OF THE INVENTION

While the way that the present invention addresses the disadvantages of the prior art will be discussed in greater detail below, in general, the present invention provides a multiple-outlet vapor-dispensing device configured to interface with an electrical receptacle such that the functionality of that outlet is substantially maintained. In accordance with one aspect of the present invention, a vapor-dispensing device is configured to connect to an electrical receptacle having a first outlet and a second outlet. The vapor-dispensing device comprises a housing having a first device outlet and a second device outlet, said housing being attachable to the first outlet and the second outlet.

BRIEF DESCRIPTION OF THE DRAWINGS

A more complete understanding of the present invention may be derived by referring to the detailed description and claims when considered in connection with the Figures, where like reference numbers refer to similar elements throughout the Figures, and:

DETAILED DESCRIPTION OF EXEMPLARY EMBODIMENTS OF THE INVENTION

The following description is of exemplary embodiments of the invention only, and is not intended to limit the scope, applicability or configuration of the invention in any way. Rather, the following description is intended to provide a convenient illustration for implementing various embodiments of the invention. As will become apparent, various changes may be made in the function and arrangement of the elements described in these embodiments without departing from the scope of the invention as set forth in the appended claims. For example, in the context of the present invention, the method and apparatus hereof find particular use in connection with air freshening vaporizer systems. However, generally speaking, various volatizable materials such as insect repellants, deodorizers, sanitizers, and/or the like are suitable for use in accordance with the present invention.

In general, the present invention provides a multiple-outlet vapor-dispensing device (e.g., a dual-outlet air-freshener) configured to interface, for example, with standard dual-outlet, quad-outlet, or such other electrical receptacles, to substantially maintain (or, indeed, augment) the functionality of the electrical receptacle with which the vapor-dispensing device interfaces.

Figure 1:
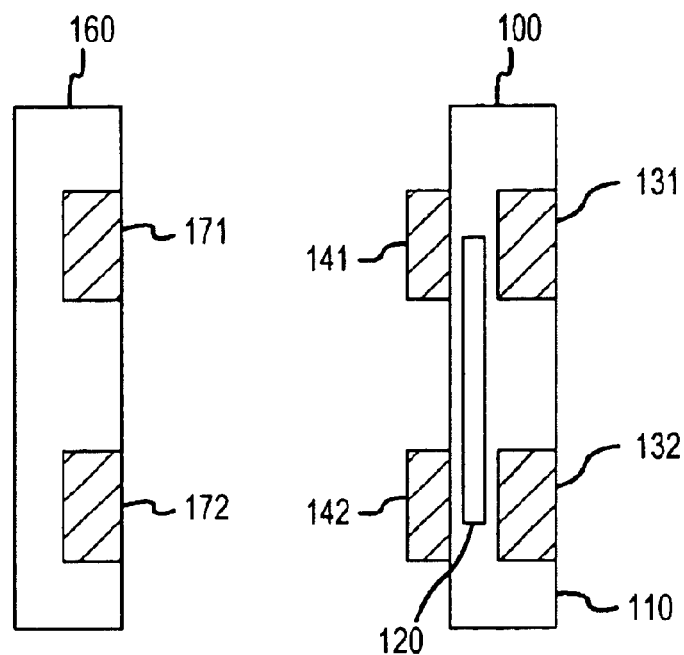
FIG. 1 illustrates in block diagram format an exemplary vapor-dispensing device in accordance with an exemplary embodiment of the present invention.

FIG. 1 illustrates, schematically, an exemplary vapor-dispensing device 100 configured to attach to an electrical receptacle 160. In general, vapor-dispensing device 100 suitably comprises a housing 110, at least one plug 141, two device outlets 131 and 132, and a fragrance delivery system 120.

Figure 2:
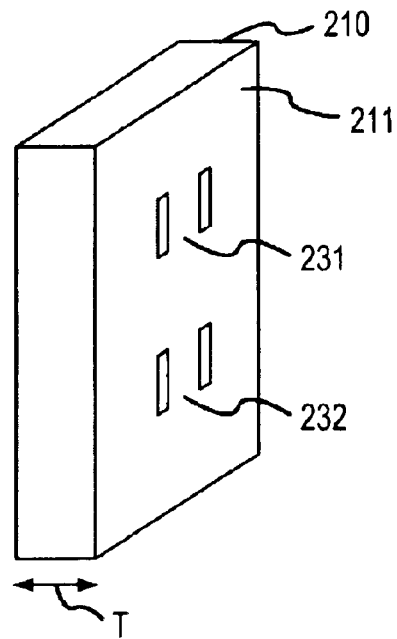
FIGS. 2 and 3 illustrate perspective views of exemplary housings in accordance with an exemplary embodiment of the present invention.
Figure 3:
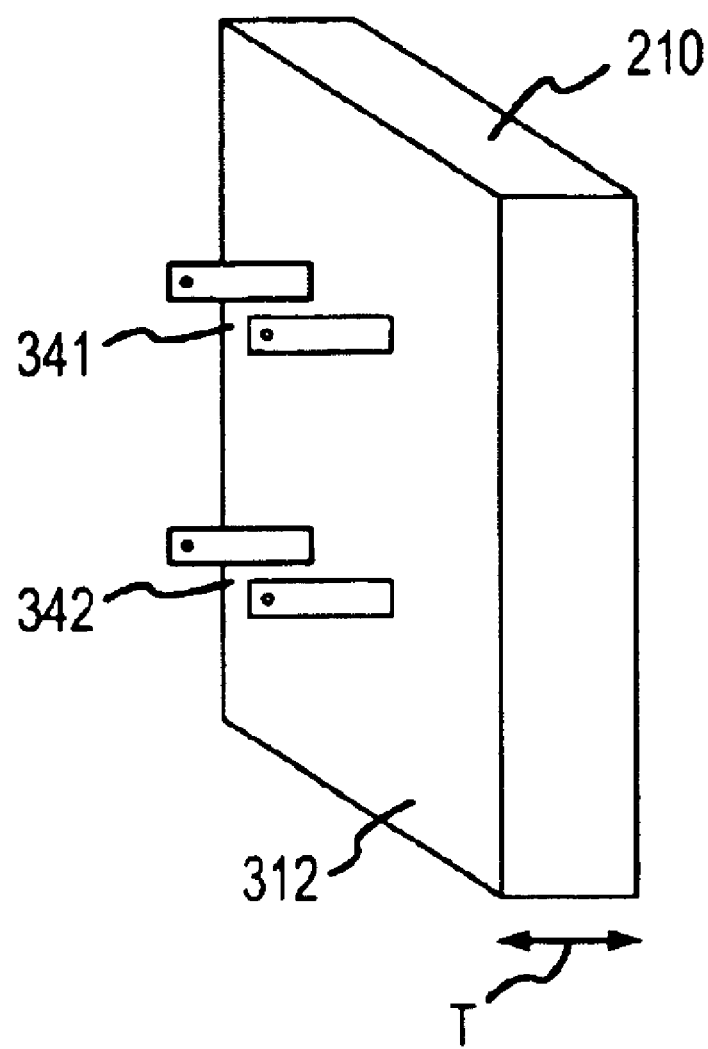

With reference to FIGS. 1, 2, and 3, and in accordance with an exemplary embodiment of the present invention, housing 210 comprises a front surface 211 and a back surface 312 separated by a thickness T. The front 211 and back 312 surfaces may generally conform to the geometry of the mating electrical receptacle 160 (and/or a face-plate associated with electrical receptacle 160), or may have any convenient shape. For example, a rectangular housing 210 may be configured to be approximately the same size as a standard rectangular wall plate for a duplex electrical receptacle (e.g., 160). The use of approximately similar dimensions for the height and width of housing 110 as on electrical receptacle 160, and the use of a narrow thickness T, aids in reducing the visibility (or increasing the "discreteness") of vapor-dispensing device 100. The thickness T may be selected in accordance with any suitable design standards. In accordance with one embodiment, for example, T is between 1.0 and 8.0 cm, preferably less than about 5.0 cm. In accordance with another embodiment, T is less than about 3.0 cm, preferably about 2.5 cm.

In accordance with one embodiment of the present invention, vapor-dispensing device 100 is configured such that, when connected to electrical receptacle 160, vapor-dispensing device 100 generally mimics a standard wall outlet plate so as to make the device less noticeable to those in the vicinity of the device and to allow functional access to one or more outlets of electrical receptacle 160.

In this regard, while the illustrated embodiment is characterized by a generally rectilinear shape, it will be understood that the present invention is not so limited. In various exemplary embodiments, the front 211 and back 312 surfaces may be different in height and width from each other, and/or from the electrical receptacle 160. For example, housing 110 may be approximately the size of a duplex electrical receptacle and yet be attached to one half of a four-plex electrical receptacle (see, e.g., FIG. 7). Furthermore, the housing may be configured with various fanciful shapes such as hearts, stars, and the like.

Housing 110 may be configured in various ways for attachment to electrical receptacle 160. In an exemplary embodiment of the present invention, housing 110 is configured to be attachable to electrical receptacle 160 via one or more plugs (e.g., plugs 141 and 142 shown in FIG. 1). More particularly, with reference to FIG. 3, a first plug 341 is suitably configured to extend from the back surface 312 of housing 210. A second plug 342 may also be configured to extend from the back of surface 312.

In the illustrated embodiment, first and/or second plug(s) 341 and 342 comprise conventional (and/or standardized) two prong plug(s) configured to be inserted into a standard duplex electrical receptacle. In general, however, the plugs may comprise any suitable male or female component (whether electrically functional or non-functional) configured to interface with corresponding structure within electrical receptacle 160.

Housing 110 may also be attached to electrical receptacle 160 via a suitable fastener (e.g., a conventional screw) located, for example, at the center or ends of the electrical receptacle. In another example, clips, Velcro brand fasteners, snaps, and/or the like may be suitably used to attach housing 110 to electrical receptacle 160.

Device outlets 131 and 132 are generally configured to mirror the functionality provided by the type (or types) of outlets 171 and 172 disposed within receptacle 160. The use of device outlets 131 for electrical needs thereby increases the inconspicuousness of vapor-dispensing device 100. For example, the illusion that vapor-dispensing device 100 is merely a typical outlet is maintained by allowing other devices (e.g., lamps, televisions, clocks, etc.) to be plugged into the same outlet. For example, outlets 171 and 172 may correspond to standard two-pronged electrical AC outlets found in many homes. In this case, it may be advantageous to likewise configure housing 110 to include standard two-pronged electrical outlets 131 and 132 which substantially correspond in location in geometry to that provided by receptacle 160.

Device outlets 131 and 132 may be electrically coupled to corresponding outlets 171 and 172, or may configured with any suitable electrical topology that provides the desired functionality of device 100. For example, a single plug 141 may be configured to be electrically coupled to more than one device outlet (e.g., 131 and 132) in housing 110. Furthermore, additional plugs may be configured, in various combinations, to be electrically coupled to one or more device outlet(s). In one exemplary embodiment of the present invention, first plug 341 is configured to provide power from first receptacle outlet 171 to two or more device outlets (e.g., 131 and 132). In another exemplary embodiment of the present invention, first plug 341 is configured to provide power from receptacle outlet 171 to first device outlet 231, and second plug 342 is also configured to provide power from receptacle outlet 172 to device outlet 232.

Furthermore, one or more plugs may be non-functional (or "dummy" plugs). Such non-functional plugs, which may comprise any suitable plastic or other insulating material, may provide structural support of the vapor-dispensing device. Alternatively, a metallic material may be used for the non-conducting plugs to the extent that the non-functional plug is configured such that a circuit is not formed by that plug.

Figure 4:
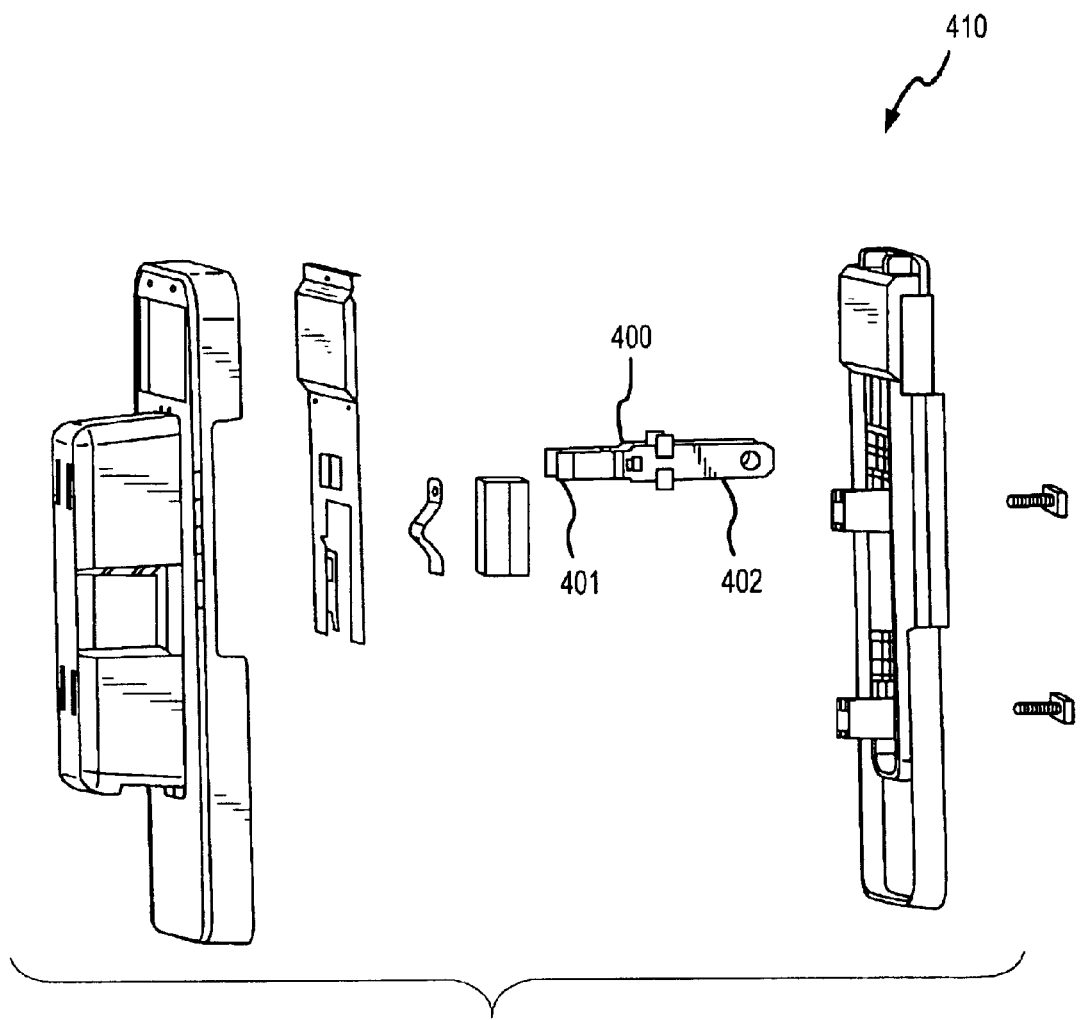
FIG. 4 illustrates an exemplary electrical coupling device in accordance with an exemplary embodiment of the present invention.

As mentioned above, a device outlet may be configured to directly couple to a corresponding outlet in the receptacle. In this regard, FIG. 4 illustrates an exemplary electrical coupling 400 for use in a vapor-dispensing device housing 410. Electrical coupling 400 may comprise a metal structure having a plug end 401 and a device outlet end 402. The metal structure may be a unitary structure for each current path. Plug end 401 is configured for insertion in a suitable electrical receptacle and for formation of an electrical contact therewith. Device outlet end 402 is configured for receiving a plug and forming an electrical contact therewith. In another example, plug end 401 and device outlet end 402 may be connected by a wire or other suitable electrical path (e.g., conductive traces and the like).

With further reference now to FIGS. 1 and 2, device outlet 231 may be configured to be substantially flush with front surface 211. In other exemplary housing structures, device outlet 131 may be raised or otherwise non-planar with front surface 211. Device outlets 131 and 132 may be configured to receive various types of plugs as described below with reference to FIG. 8.

Figure 5:
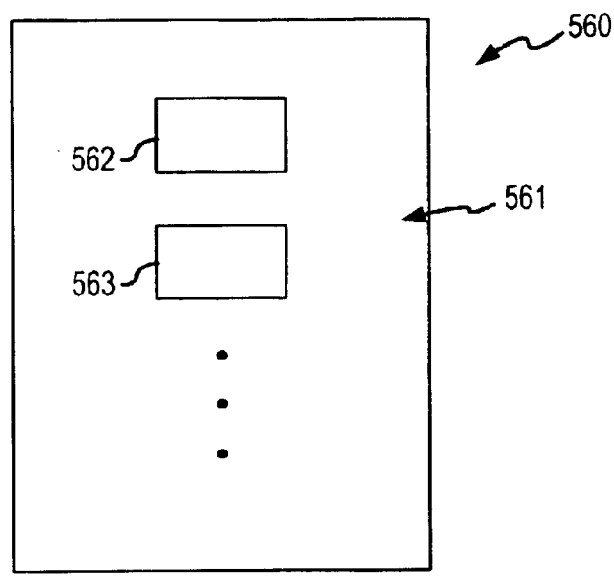
FIG. 5 illustrates an exemplary electrical receptacle in accordance with exemplary embodiments of the present invention.

With reference now to FIGS. 1 and 5, electrical receptacle 160 may include any standard wall outlet fixture configured for receiving electrical plugs, such as plugs provided on one end of a power cord. In the illustrated embodiment, electrical receptacle 160 comprises two or more outlets 171 and 172. FIG. 5 illustrates an exemplary electrical receptacle 560 comprising a face plate 561 and two or more outlets (e.g., 562, and 563). Face plate 561 may comprise openings suitable for exposing one or more outlets. Various styles and designs of face plates may be used.

Figures 6, 7:
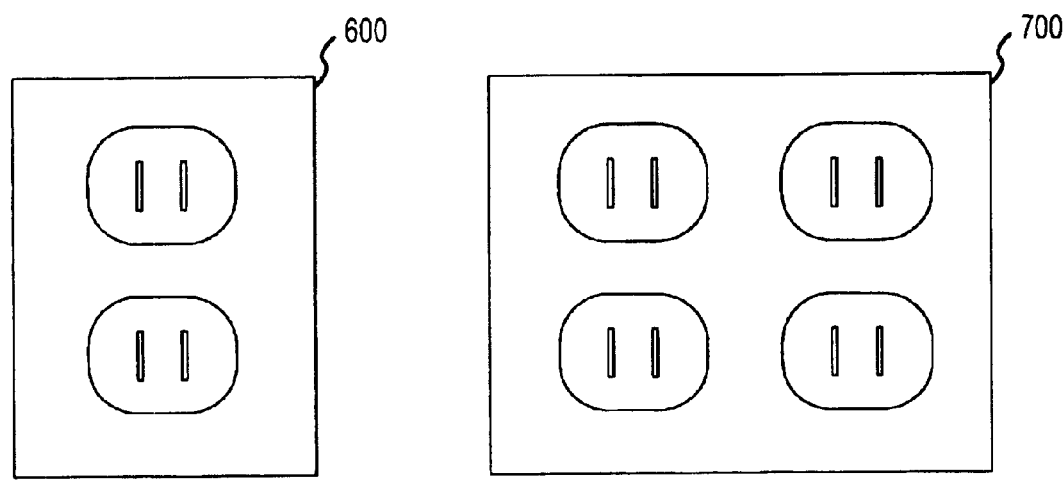
FIGS. 6 and 7 illustrate exemplary outlet arrangements in accordance with exemplary embodiments of the present invention.

Electrical receptacle 160 may also comprise various numbers of outlets. With reference to FIG. 6, an exemplary dual outlet electrical receptacle 600 is illustrated. With reference to FIG. 7, an exemplary four outlet electrical receptacle 700 is illustrated. Other outlet numbers and arrangements may suitably be used. The number of device outlets 131 may not correspond to the number of electrical receptacle outlets provided on the housing. For example, two electrical receptacle outlets may be covered and four device outlets provided for use. Thus, vapor-dispensing device 100 may serve as an adapter splitting one plug into two or more device outlets.

Figure 8:
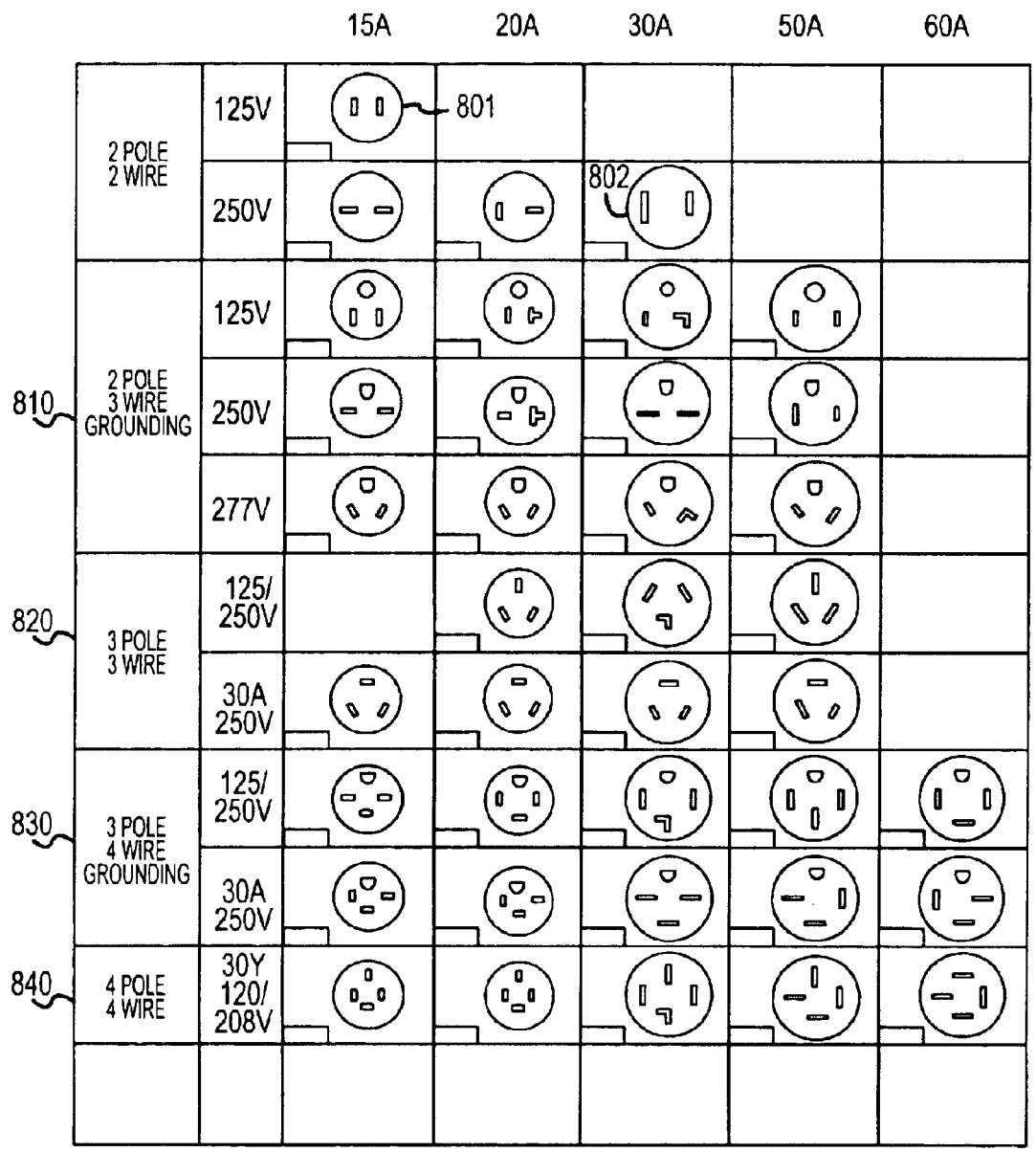
FIG. 8 illustrates exemplary outlets in accordance with exemplary embodiments of the present invention.

Electrical receptacle outlets and/or device outlets may comprise any suitable configuration of poles and/or grounding. In this regard, FIG. 8 illustrates exemplary configurations of pole/grounding connections in exemplary outlets. For example, outlets 131 and 171 may comprise a two pole outlet 801. In another example, a 30 amp, 250 volt rated outlet may comprise a two pole outlet 802 where one pole has a larger receiving socket than the other. Additional exemplary outlet embodiment sets 810 and 820 each have outlets comprising three receiving sockets. For example, the outlet may include one of the two pole, three wire grounding outlets 810 or one of the three pole, three wire outlets 820. Furthermore, the outlet may have four sockets, such as the three pole, four wire grounding outlets 830 or four pole four wire outlets 840. In general, the outlets may comprise any type of outlet, whether powered or not. For example, the present invention is applicable to receptacles including one or more of communications outlet types, such as a telephone jacks, Ethernet jacks, coaxial jacks, and the like. Furthermore, it is not necessary for the receptacle to include only one type of outlet. The present invention comprehends any number and combination of outlets.

Vapor-dispensing device 100 also comprises a fragrance delivery system 120 configured to enhance the evaporation of a volatizable material. Fragrance delivery system 120 may be a part of housing 110 or may suitably be configured to attach to housing 110. In either embodiment, the fragrance delivery system is configured to enable use of the one or more device outlets 131 while also functioning to deliver fragrance.

In one exemplary embodiment of the present invention, the housing may be configured to facilitate heating of a volatizable material provided by fragrance delivery system 120. Housing 110 may comprise a heating element that suitably assists in vaporizing the volatizable material from fragrance delivery system 120. In this embodiment, the heating element may comprise a resistance-type heating element, though generally speaking, any mechanism that assists in volatizing the material from fragrance delivery system 120 may, typically through kinetic energy, be a "heating element". Additionally, momentarily, it should be noted, that in various alternative embodiments of the present invention, vapor-dispensing device 100 may be a "passive" vaporizer. Stated otherwise, the material of fragrance delivery system 120 may volatize merely by exposure to ambient conditions (e.g., room temperature). Thus, no heating element may be required. Fragrance delivery system 120 may also comprise other material delivery systems such as, for example, gel and/or membrane type fragrance dispensers. In such cases, the volatizable material might be in a "gel" and/or semi-permeable solid form that dispenses through mechanisms such as sublimation. Thus, it should be appreciated that any fragrance delivery mechanism now known or as yet unknown in the art can suitably be configured to be used in the present invention.

Heating elements may be suitably configured to be adjustable to varying temperatures. In accordance with various aspects of the present invention, a switch may also be suitably configured to control the varying temperature of a heating element. Similarly, dispensers having variable temperature control can provide the ability to increase or decrease the amount of fragrance dispensed depending on the intensity and strength of heat provided by heating element, user desired performance, room size and the like.

In various other examples, housing 110 and fragrance delivery system 120 might have different roles, i.e., housing 110 and fragrance delivery system 120 may act cooperatively to provide heat for volatilization and/or fragrance and heating elements may be reversed on the structures. Further still, alternatively, vapor-dispensing device 100 may comprise a single, unitary structure with all vaporization elements of fragrance delivery system 120 integrated into housing 110.

Figure 9:
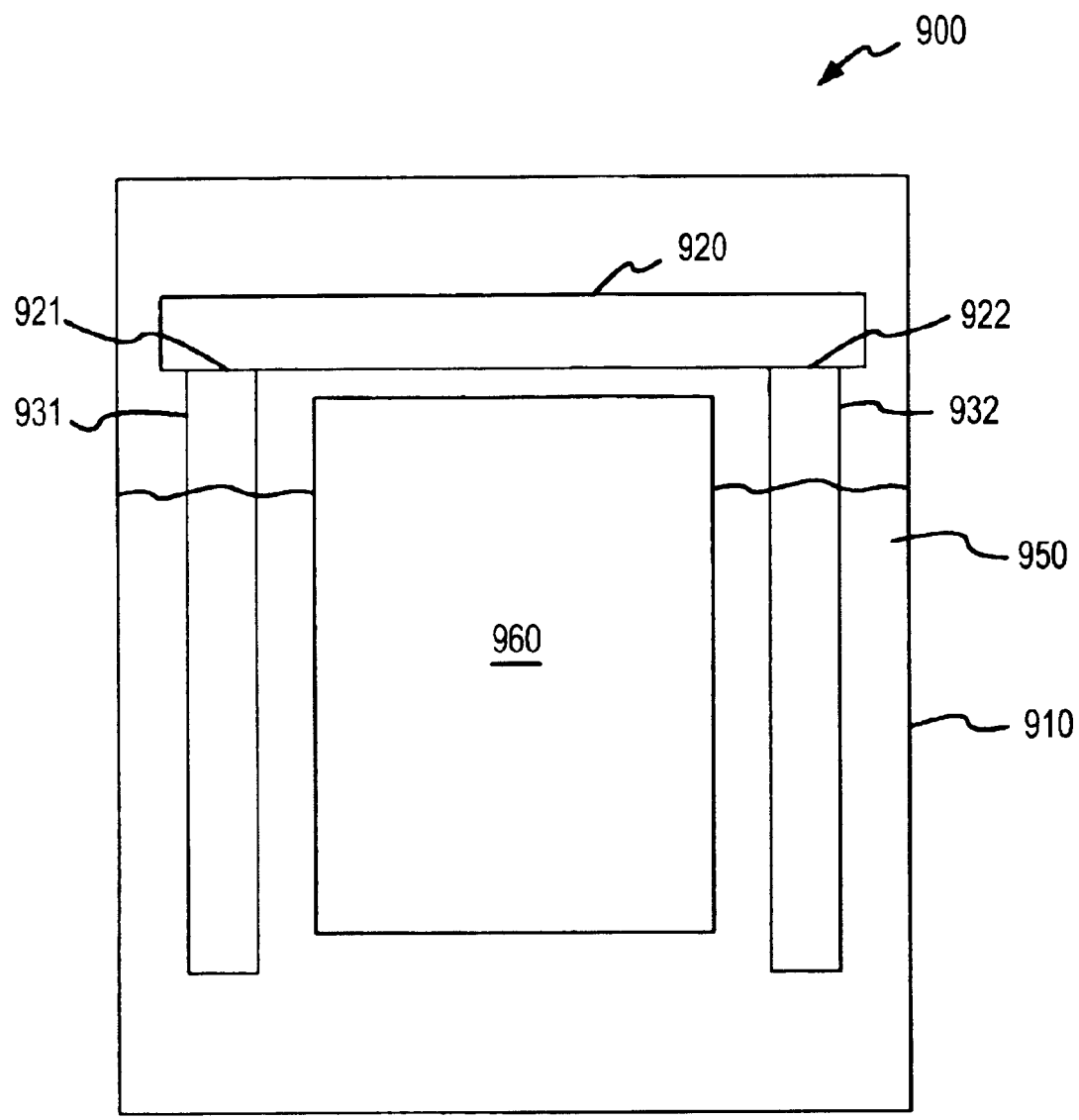
FIG. 9 illustrates an exemplary fragrance delivery system in accordance with exemplary embodiments of the present invention.

FIG. 9 illustrates an exemplary fragrance delivery system 900. Fragrance delivery system 900 comprises a chamber 910, an eminator 920, a first wick 931 and a second wick 932. Chamber 910 is configured to contain a volatizable material 950 provided therein. For example, chamber 910 may be configured as a liquid filled reservoir, which is functionally similar to the reservoir bottles of now known vaporizer refill bottles. In such configurations, chamber 910 has a hollow section filled with, for example, a scented oil that is vaporized from fragrance delivery system 120. In the illustrated embodiment, a central region 960 of chamber 910 is cut-away to facilitate access to the receptacle.

Eminator 920 is configured to receive volatizable material 950 and to facilitate the dispersion of said material to the surrounding environment. For example, eminator 920 may draw volatizable material into a region that can be heated by a heating element. Eminator 920 may be configured to attach at a first point 921 to a first wick 931 and to attach at a second point 922 to a second wick 932. Therefore, eminator 920 may receive volatizable material through such mechanisms as the wicking of volatizable material 950 from chamber 910. First wick 922 and second wick 932 may be made, for example, of a porous material such as graphite, porous plastic or other fibrous materials.

That being said, in accordance with the presently described illustrative embodiment, fragrance delivery system 120 is suitably configured to have the shape and size of housing 110 such that it can be assembled to housing 110 in a manner that facilitates the minimizing of the likelihood of being noticed by those in the vicinity of vapor-dispensing device 100. For example, in the present exemplary embodiment, fragrance delivery system 120 has a substantially rectangular shape corresponding to housing 110 (similar to a standard wall outlet plate). Additionally, the presently described embodiment may suitably exhibit improved stability, and/or facilitate the interaction of heating elements (to the extent that heating elements are included in vapor-dispensing device 100) with fragrance delivery system 120.

Notwithstanding the nature of receptacle 120—i.e., whether and to what extent receptacle 120 is configured to supply electrical current—delivery system 900 may be passive, active, or selectably switched between active and passive modes. The term "passive" in this context, as applied to delivery devices, refers to those devices which substantially depend upon ambient conditions to deliver a fragrance or otherwise give rise to a modification of the environment. Such ambient conditions include, for example, ambient thermal conditions (e.g., wall surface temperature and air temperature) and ambient air flow, (e.g., air flow resulting from free convection as well as the movement (if any) of fans, individuals, and other entities within the environment). The term "active" in this context refers to devices that are not passive, e.g., devices which employ integrated fans, heating elements, and other such devices.

In the event that delivery device 900 is an active device, any power source required by the device may be intrinsic to receptacle 120, e.g., the 120 V source of a standard wall outlet, or extrinsic to receptacle 120, e.g., supplied by a battery, solar cell, or other such device incorporated into or otherwise associated with delivery device 210.

Alternatively, power may be supplied by a combination of intrinsic and extrinsic sources and/or may be incorporated into a refill component, described in further detail below.

Delivery device 900 suitably includes one or more removeably attached refill components. That is, referring to FIGS. 10A–10C, it may be advantageous for delivery device 900 to include components that are integral to the delivery device itself as well as one or more refill components 1002 (or simply "refills") that can be replaced by the user. In the event delivery device 900 is an air freshener device, for example, a depleted refill component 1002 may removed from device 900 and replaced by a new refill containing fragrant oil, wax, gel, or the like. The refill suitably includes a refill body and a volatizable material provided therein.

In accordance with one aspect of the present invention, a refill component is provided which allows vapor-dispensing device to mimic an electrical receptacle. For example, a refill may be configured to be inserted behind the front surface of the device such that it is substantially concealed by the front surface. In accordance with one aspect of the present invention, the refill has a perimeter that is encompassed by the perimeter of the housing.

Figures 10A, 10B, 10C:
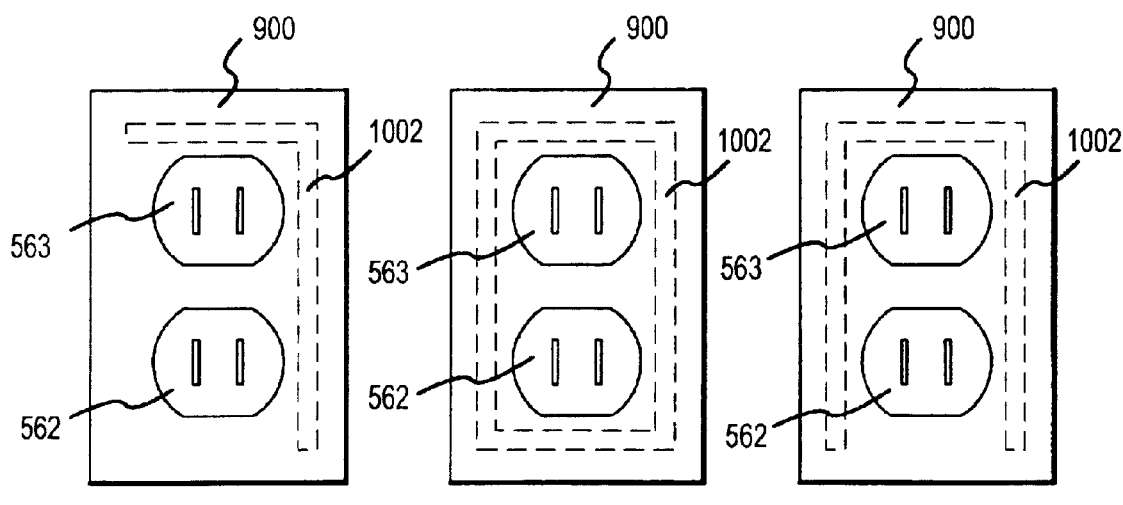
FIGS. 10a, 10b and 10c illustrate exemplary refill configurations in accordance with the present invention

In accordance with another aspect of the present invention, the refill is configured such that it does not significantly obstruct the receptacle's outlet pattern (e.g., outlets 562 and 563). In one embodiment, for example, this is accomplished by providing a refill component 1002 that at least partially surrounds one or more outlets on the receptacle (variously shown in FIGS. 10A–10C). In the event that the delivery device is used in connection with a standard electrical receptacle, it is desirable for refill 1002 to encompass two or more sides of the outlet pattern (FIG. 10A). To the extent that it is advantageous to supply the greatest possible volume of volatizable material, the refill may be configured as a rectangular ring that completely surrounds the outlet pattern (FIG. 10B). Alternatively, the refill may be configured in a 'U' shape to allow refill 1002 to be slideably removed from the device (FIG. 10C).

The present invention has been described above with reference to various exemplary embodiments. However, many changes, combinations and modifications may be made to the exemplary embodiments without departing from the scope of the present invention. For example, the various components may be implemented in alternate ways. These alternatives can be suitably selected depending upon the particular application or in consideration of any number of factors associated with the operation of the system. In addition, the techniques described herein may be extended or modified for use with other types of devices. These and other changes or modifications are intended to be included within the scope of the present invention.

What is claimed is:

1. A vapor-dispensing device configured to connect to an electrical receptacle having a first outlet and a second outlet, said vapor-dispensing device comprising:
   a housing having a first device outlet and a second device outlet;
   a first plug electrically coupled to said first device outlet and configured to be inserted in the first outlet of the electrical receptacle;
   a second plug electrically coupled to said second device outlet and configured to be inserted in the second outlet of the electrical receptacle;
   a fragrance delivery system comprising a chamber having a volatizable material provided therein and means for volatizing said volatizable material; and
   a refill component removeably attached to said fragrance delivery system, said refill component including a refill body and a volatizable material provided therein.

2. The device of claim 1, wherein said fragrance delivery system comprises:
   an eminator having a first contact point and a second contact point remote from said first contact point, wherein a first wick is coupled to said eminator at said first contact point, and a second wick is coupled to said eminator at said second contact point; and
   said first and second wicks being at least partially immersed in said volatizable material and positioned adjacent opposite sides of said first device outlet.

3. The device of claim 2, wherein said eminator and said first and second wicks are enclosed within said refill component.

* * * * *